United States Patent [19]
Blonder et al.

[11] Patent Number: 5,967,305
[45] Date of Patent: Oct. 19, 1999

[54] DENTAL IMPLANT COMPONENT PACKAGE AND HOLDER

[76] Inventors: Howard Blonder, 10933 Lakewood Blvd., Downey, Calif. 90241; Kenneth K. Krueger, 28652 La Dera, Laguna Niquel, Calif. 92667; Gregory T. Anascavage, 2 Atlanta, Irvine, Calif. 92620; Gregory M. Smith, 18168 Sharon La., Yorba Linda, Calif. 92886

[21] Appl. No.: 08/932,160

[22] Filed: Sep. 17, 1997

[51] Int. Cl.$^6$ ................................................. B65D 85/30
[52] U.S. Cl. ........................................... 206/63.5; 206/486
[58] Field of Search ......................... 433/173; 206/63.5, 206/438, 368, 477, 478, 486, 490

[56] References Cited

U.S. PATENT DOCUMENTS 5,538,428  7/1996  Staubli ............................... 206/63.5 X Primary Examiner—Jacob K. Ackun

[57] ABSTRACT

A dental implant package and holder is provided comprising a resiliently flexible envelope within a component box and a holder for holding a dental implant or implant component inside the resiliently flexible envelope. The resiliently flexible envelope is so configured and constructed that when it is contained in the component box it is under compressive stress. When the top of the component box is opened such stress is relieved by extension of the envelope through the open top. In one form of the invention, the component may be attached to a special holder for the component. The holder is an elongate memeber having a length and proximal and distal ends, a width and a thickness, the width being greater than about ten times the thickness, the length being from about three-fourths inch to one inch and being greater than about four times the width. The holder is constructed and configured to define a generally circular component holding aperture through the thickness thereof adjacent the proximal and a V-shaped entry communicating with the aperture and extending to the proximal end of the holder.

2 Claims, 1 Drawing Sheet

DENTAL IMPLANT COMPONENT PACKAGE AND HOLDER

FIELD OF THE INVENTION

This invention relates to dental implant technology

BACKGROUND OF THE INVENTION

Dental implant technology is well developed and there is a large body of literature describing this technology in technical reports, professional literature and patents. Indeed, within the past decade, this has become a very crowded art.

The prior art discloses a vast array of dental implant components. For convenience, the term "implant components" or simply "components" will be used herein as a shorthand reference to all of the components of a dental restoration or other procedure that involves the implantation of a pin, screw or other device into the jaw of a patient, including the components attached thereto, such as abutments, copings, prostheses and attaching components such as screws, pins, washers, etc. The reader is referred to the following United States Patents to illustrate, in general, a few of the types of components that may be used U.S. Pat. No. 5,476,382 to Daftary, U.S. Pat. No. 5,431,576 to Daftary, U.S. Pat. No. 5,431,567 to Daftary, U.S. Pat. No 5,030,096 to Hurson, et.al., and 4,856,648 to Krueger The components used in dental implant technology are very small, so small, indeed, that in many instances it is impossible visually to distinguish between different sizes, and sometime it is difficult to distinguish even between different components. Magnification and/or the use of calipers or other measuring devices are often necessary to ascertain exactly the type and size of the component.

A great variety of types and sizes of components must be kept on hand to assure that the dentist or oral surgeon has the right type of component in the right size to treat a patient. Sometimes, a preliminary procedure or examination enables the doctor to determine in advance the type and size of a dental implant, abutment, coping, etc., that will be required; however, a change of type or size may be required while a procedure is being carried out as a result of the discovery of a problem not previously known, or some other circumstance which cannot be fully determined until the procedure begins. Often, Of course, the type or size of a dental implant component is unknown or cannot be determined until a dental or surgical procedure is begun. In all cases, however, it is important that the doctor have on hand a substantial number of components to assure that the proper components are on hand.

Dental implant components, being very small, are difficult to handle. Many are so small that extremely well developed manual dexterity is required simply to hold them in a given position and special holding tools are required to use them.

Efforts have been made to provide packaging and holders to enable the doctor to identify, select and/or to hold the component and to use the component in a dental or surgical procedure, U.S. Pat. No 4,856,648 to Krueger, U.S. Pat. No. 5,290,171 to Daftary and U.S. Pat. No. 5,030,96 to Hurson, et. al., are exemplary of such efforts.

A companion problem is that of maintaining sterility of the dental implant component. Such components are frequently pre-sterilized by the manufacturer in a sealed package or envelope. Sterility is reliably obtained and reasonably assured so long as the sterile package is not opened or damaged. The dentist often finds it difficult to handle these small components and yet maintain sterility. The component must be removed from the sterile package and transferred to the opening in the patient's mandible or maxilla directly or by way of a sterile surgical holder or instrument. Removing the small component from the package while maintaining sterility is a serious inconvenience. Facets of this problem, and examples of the types of components of concern, are addressed in the following U.S. Pat. Nos. 4,976,617 to Carchidi; 4,941,227 to Sussman, 5,062,800 to Niznick, 5,290,171 to Daftary, et. al., 5,368,160 to Leuschen, et. al., 5,538,428 to Staubli, 5,558,230 to Fischer, et. al.; and 5,582,299 to Lazzara et. al, One facet of the present invention addresses this problem.

Notwithstanding the many efforts in this crowded art to provide the doctor with dental implants and dental prostheses and components thereof in a way that will permit quick and certain identification and provide means for handling dental implant components, there remains the need for a compact orderly system and apparatus to minimized space requirements in the doctor's operating room and, at the same time, present the components in a convenient manner for identification, handling, and use. This invention meets this need more efficiently and more conveniently that any system or apparatus of which the inventors are aware.

SUMMARY OF THE INVENTION

The present invention is embodied in a resiliently flexible envelope in a component box, a dental implant or dental prosthesis or a component of a dental implant or dental prosthesis and a holder for the component inside the resiliently flexible envelope. The resiliently flexible envelope is so configured and constructed that when it is contained in the component box it is under compressive stress and when the top of the component box is opened such stress is relieved by extension of the envelope through the open top In one form of the invention, the component may be attached to a special holder for the component. The holder is an elongate member having a length and proximal and distal ends, a width and a thickness, the width being greater than about ten times the thickness, the length being from about three-fourths inch to one inch and being greater than about four times the width. The holder is constructed and configured to define a generally circular component holding aperture through the thickness thereof adjacent the proximal and a V-shaped entry communicating with the aperture and extending to the proximal end of the holder.

DESCRIPTION OF THE PREFERRED EMBODIMENTS

Figure 1:
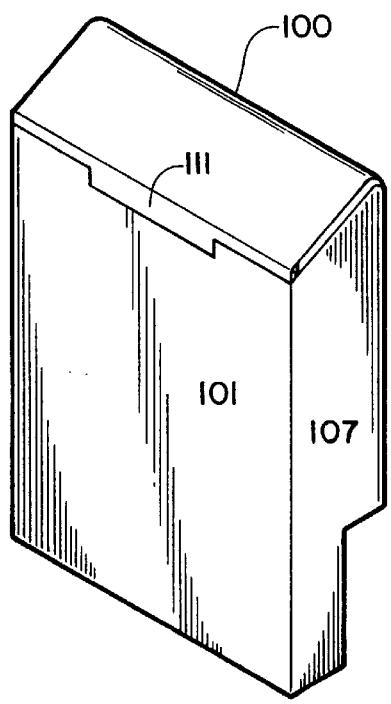
FIG. 1 is a perspective view of one component packages with which the present invention is very conveniently used.

The following description and the exemplary embodiments depicted in the drawings disclose the best form of the invention presently known to the inventors. Neither the description nor the drawings are, however, limiting. There are many facets to the invention. The invention can be made of a combination of any of a large number of materials. The configuration of each of the individual components may vary considerably, so long as the relationship permits display and use. Indeed, many variations and adaptations can be made within the spirit of the invention and without departing from the claims. Thus, the specification and drawings are exemplary, not limiting.

In one preferred form of the invention, the individual component box 100 shown in FIG. 1 is a stepped back individual component box. The invention may, however, comprise any other individual component holder that is of a material, size and shape to function as described below.

The stepped back individual component box 100 comprises a full front panel 101, an upper back panel 102, a forwardly extended. (toward the front panel) step 103, and a lower stepped panel 104 secured in box form by a bottom 105 and ends 107 and 108. A lid 109 is secured by a flexible hinge line 110 to the top of the upper back panel 102 and provided with a tab 110 for permitting opening of the lid. The lid is normally held closed by a label, described below, which must be torn to permit opening of the box.

The stepped back, individual component box is secured in the closed position by a tamper indicating adhesively bonded label 112 which extends at least over a large portion of the front panel 101 and over at least a portion of the lid 109 so that the package cannot be opened without tearing the label. It is, therefore, impossible to tamper with the contents of the stepped back individual component box without indicating such tampering. In the preferred form, the label covers substantially the entire front panel and the lid and extends downwardly onto the upper back panel.

Indicia are printed on the label identifying the product, providing required information, dimensions, etc. as appropriate to the particular component contained in the stepped back individual component box. In particular, because the components are so small that individual sizes may appear to be the same and some components may appear to be the same to the unaided eye, specific indicia are printed on the label to be displayed on the front and/or top of the stepped back individual component box to identify both the product and the size.

The box is desirably made of a transparent plastic, e.g., an acrylic polymer such as polymethyl methacrylate, or polystyrene, however, the material is not critical and any material that is sufficiently strong and light may be used. It may be desirable to use a polymer which is sufficiently flexible in thin sections to form the hinge line 110; however, normally the label forms the hinge. Since only a few flexes are required, however, to close the stepped back individual component box and one to open it, great flexibility is not required.

Figure 2:
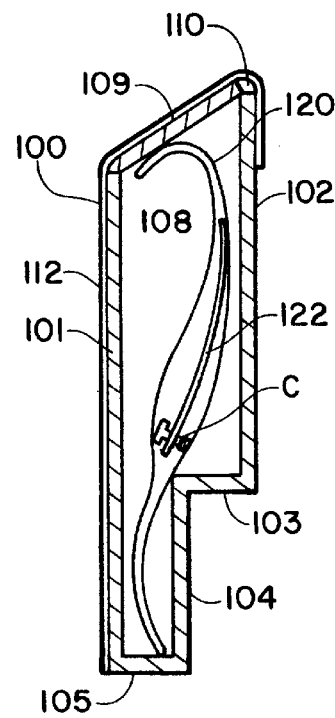
FIG. 2 is a side view, in partial cross-section, showing the component package with a resiliently flexible envelope package enclosing a sterile dental implant component mounted on a holder in the package, the package being closed.
Figure 3:
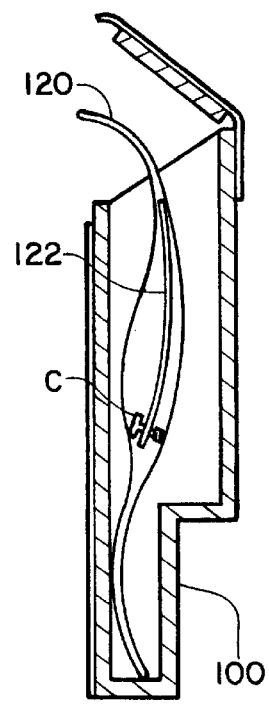
FIG. 3 is a side view of the package depicted in FIG. 2 with the top lid of the component package open and the edge of the resiliently flexible envelope enclosing a sterile dental implant component on a hold, the envelope extending upwardly to enable the user to grasp the same and remove it from the individual component package.

In one advantageous aspect, the individual component C, as shown in FIGS. 2 and 3, is sealed in an envelope 120 or other package formed of a sterilizable transparent resilient polymer. It will be seen irk FIG. 2 that the envelope can be bent sufficiently to place it entirely in the stepped back individual component box. As shown in FIG. 1, once the lid of the stepped back individual component box is opened the envelope springs upwardly to extend from the box so as to permit the user conveniently to grasp the envelope and remove it from the box without damaging the envelope, thereby risking contamination. The envelope can then be opened by tearing or using sterile scissors, etc. and the component removed using a sterile tool or holder, The container and display system of this invention thus, in its preferred embodiment, comprises a resiliently flexible envelope in each of the component boxes and a dental implant or a dental prosthesis or a component of a dental implant or dental prosthesis inside the resiliently flexible envelope. The resiliently flexible envelope is so configured and constructed that when it is contained in the component box it is under compressive stress and when the top of the component box is opened such stress is relieved by extension of the envelope through the open top of the individual component container.

The envelope may be made of any transparent polymer which is flexibly resilient enough to be folded and yet to retain sufficient resilience to return to an extended position when the box is opened. The material should also be capable of being sterilized. Sterilization can be accomplished by heat or radiation, or in any manner which is reliable. Materials such as Mylar® polyethyleneterphthalate, nylon, etc. may be used. Certain cellulose ester films as well as parchment paper may also be used to form the envelope.

Figure 4:
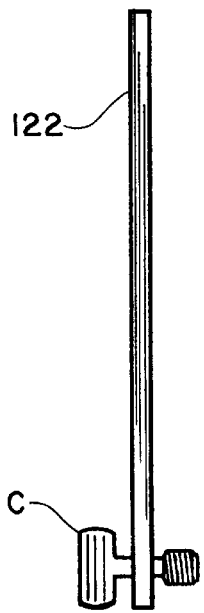
FIG. 4 is a side view of the component holder of this invention holding an exemplary component, an implant screw.
Figure 5:
FIG. 5 is a front view of the component holder of this invention, as shown in FIG. 4, showing an implant screw mounted thereto The back of the holder is a mirror image of the front.
Figure 6:
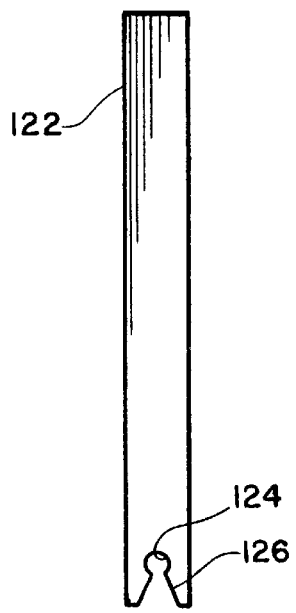
FIG. 6 is a front view of the component holder of this invention, as shown in FIG. 4, without a component mounted thereto. The back of the holder is a mirror image of the front.

A very important and useful, and yet elegantly simple, feature which, alone, is the sole invention of one of the inventors, is shown in FIGS. 4, 5 and 6. The component C is held by a holder 122. A side view of the holder 122, as shown in FIG. 4, depicts the holder attached to the component C, an implant screw being the exemplary dental implant component. The front view of the holder 122 shown in FIG. 5 attached to the component C and the front view without the component depict the elegantly simple grasping structure of the holder The holder is constructed of a resilient, semirigid polymer and configured to define an aperture 124 for receiving a dental implant or prosthesis or a component thereof, e.g., the exemplary dental implant screw C, and an entry structure 126 which is of a size and shape to permit the implant, prosthesis or component thereof to be inserted into the aperture 124 against the resilient bias of the material of the holder 122. The component holder is attached to and extends from the component. The holder is constructed of a resilient, semi-rigid polymer configured to define an aperture for resiliently receiving and hold the component. The holder also defines entry structure communicating with the aperture constructed and configured to permit the component to be inserted into the aperture against the resilient bias of the holder material. The material is rigid enough to enable the user, e.g., a dentist or oral surgeon, to grasp the distal end thereof, shown at the top in the Figures, with sterile gloved fingers, forceps or another grasping tool to move the component to a desired location for implantation or association with other components. The material of which the holder 122 is made is also resilient enough that the component is grasped by such resilience in the aperture 124.

In the preferred form, the holder is an elongate member having a length and proximal and distal ends, a width and a thickness, the width being greater than about ten times the thickness, the length being from about three-fourth inch to one inches and being greater than about four times the width. The holder is constructed and configured to define a generally circular component holding aperture through the thickness thereof adjacent the proximal and a V-shaped entry communicating with the aperture and extending to the proximal end of the holder.

Polymers such as nylon, polyacetal, polystyrene, polycarbonate, and many other polymers are readily formulated using known techniques to have the required rigidity and resilience.

It will be apparent from a review of the foregoing that a convenient system is provided which provides for compact storage, convenient display, ready and safe access and convenient sterile handling has been provided.

INDUSTRIAL APPLICATION

This invention is useful in dentistry and in the dental implant industry.

What is claimed is:

1. A dental implant component container and holder system for containing sterile dental implants and prostheses and components thereof for convenient use by a dentist or oral surgeon comprising, in combination:

a box for containing dental implant components that is constructed and configured to define component containing space and an openable top, a dental implant component inside the component box, and a component holder attached to and extending from the component, the holder being an elongate member having a length and proximal and distal ends, a width and a thickness, the width being greater than about ten times the thickness, constructed of a resilient, semi-rigid polymer constructed and configured to define an aperture through the thickness for resiliently receiving and holding the component and to define entry structure constructed and configured to permit the component to be inserted into the aperture against the resilient bias of the holder material.

2. A dental implant component container and holder system for containing sterile dental implants and prostheses and components thereof for convenient use by a dentist or oral surgeon comprising, in combination:

a box for containing dental implant components that is constructed and configured to define component containing space and an openable top, a dental implant component inside the component box, a component holder attached to and extending from the component, the holder being constructed of a resilient, semi-rigid polymer constructed and configured to define an aperture for resiliently receiving and holding the component and to define entry structure constructed and configured to permit the component to be inserted into the aperture against the resilient bias of the holder material and a resiliently flexible envelope in the component box, the component and holder being inside the resiliently flexible envelope, the resiliently flexible envelope being so configured and constructed that when it is contained in the component box it is under compressive stress and when the top of the component box is opened such stress is relieved by extension of the envelope through the open top.

* * * * *